ated Patent [19]

United States Patent [19]
Mizuta et al.

[11] Patent Number: 4,775,838
[45] Date of Patent: Oct. 4, 1988

[54] SENSOR WITH PERIODIC HEATING

[75] Inventors: Toshiaki Mizuta; Minoru Miyoshi, both of Yokohama; Junji Manaka, Kawasaki, all of Japan

[73] Assignees: Ricoh Company, Ltd.; Ricoh Seiki Co. Ltd., both of Tokyo, Japan

[21] Appl. No.: 836,151

[22] Filed: Mar. 4, 1986

[30] Foreign Application Priority Data

| Mar. 4, 1985 [JP] | Japan | 60-41208 |
| Mar. 4, 1985 [JP] | Japan | 60-41209 |
| Mar. 4, 1985 [JP] | Japan | 60-41210 |

[51] Int. Cl.$^4$ .............................. G01N 27/62
[52] U.S. Cl. ................... 324/468; 324/65 R
[58] Field of Search ............ 324/65 R, 65 P, 224, 324/468, 466; 340/634; 73/27 R; 338/34, 35, 23, 24

[56] References Cited

U.S. PATENT DOCUMENTS

| 4,176,311 | 11/1979 | Davis | 324/468 |
| 4,373,392 | 2/1983 | Nagamoto | 324/65 R |
| 4,404,524 | 9/1983 | Yamamoto et al. | 324/468 |
| 4,485,667 | 12/1984 | Lalauze et al. | 73/27 R |

Primary Examiner—Reinhard J. Eisenzopf
Assistant Examiner—Anthony L. Miele
Attorney, Agent, or Firm—Oblon, Fisher, Spivak, McClelland, & Maier

[57] ABSTRACT

A gas sensor includes a pair of lead strips, a sensing element preferably comprised of a metal oxide semiconductor, such as $SnO_2$, and extending between the pair of lead strips in the form of a bridge, a heater driver for supplying a heating current to at least one of the pair of lead strips, a detector for detecting a predetermined property of the sensing element, and a control circuit for controlling the operation of the heater driver and the detector. In one form of the invention, the detector is activated in a time period in which the heater driver is not activated. In another form of the invention, the pair of lead strips are connected in parallel or in series when the heater driver is to be activated. In a further form of the invention, the heater driver is normally operated periodically, but when the detector first detects a predetermined condition, the heater driver is operated continuously.

16 Claims, 7 Drawing Sheets

SENSOR WITH PERIODIC HEATING

BACKGROUND OF THE INVENTION

1. Field of the Invention

This invention generally relates to a sensing device for sensing the environmental status change, and, in particular, to a sensor for sensing the presence of a particular gas or vapor, such as alcohol, or a level of temperature or humidity. More particular, the present invention relates to a sensing device including a sensing element, the change in electrical resistance of which is utilized for sensing of a desired parameter.

2. Description of the Prior Art

A gas sensor for sensing the presence of a particular gas in the environment over a predetermined amount is widely used. A typical prior art gas sensor includes a sensing element comprised of a metal oxide semiconductor and a heat coil, which also serves as an electrode, embedded in the sensing element. Under the condition that the sensing element is heated to a predetermined temperature by the heater coil, when the sensing element absorbs at its surface a particular gas in the atmosphere, the level of the electrical resistance of the sensing element drops significantly. Thus, this may be utilized to indicate the presence of a particular gas in the atmosphere beyond a predetermined level. In the prior art device, the driving current applied to the heater coil is in the form of a pulse, thereby decreasing power consumption to allow the usage of a battery as a power source.

In the prior art device, the electrical resistance of the sensing element is detected during the time period in which the sensing element is heated. In this case, however, the driving current supplied to the heater coil partly leaks through the sensing element, and such a leak current causes an apparent reduction of an output detection signal from the sensing element. For example, if the resistance of the sensing element under normal condition exhibits approximately 1 M-ohms and it decreases to 500 K-ohms when sensing a particular gas, the application of a driving current of 2 micro-amperes to the sensing element would produce an output voltage of 2 Volts under normal condition and of 1 Volt when sensing a particular gas. However, with the presence of the above-mentioned leak current, since it is equivalent to the situation, in which a resistor having the resistance of 500 K-ohms is connected in parallel with the sensing element, so that the total resistance is approximately 333 K-ohms under normal condition and 250 K-ohms during gas detection. As a result, for the same driving current of 2 micro-amperes, the output voltage will change only from 0.67 Volts to 0.5 Volts.

SUMMARY OF THE INVENTION

In accordance with the present invention, there is provided a sensing device wnich includes a sensing element which changes its electrical resistance depending on the status of its environment and heating means for heating said sensing element periodically, whereby the electrical resistance of the sensing element is detected during a time period in which the sensing element is not heated by the heating means. In this manner, in accordance with the present invention, the sensing device is so structured to utilize the memory effect of the sensing element. In other words, when sensing a particular status in the environment, the sensing element is heated for a short period of time while being exposed to the environment, and the sensing element retains the condition acquired during sensing for a predetermined time period. And, in accordance with the principle of the present invention, a driving current is applied to the sensing element at such a timing in which no driving current for heating is applied. Thus, the output signal obtained from the sensing element is least affected.

In accordance with another aspect of the present invention, there is provided a sensing device which includes a sensing element, heating means for heating the sensing element, and detecting means for detecting the electrical resistance of the sensing element, wherein a first driving current in the form of a pulse having a first time period is periodically applied to the heating means during a normal sensing operation and a second driving current in the form of a pulse having a second time period longer than the first time period is applied to the heating means when the detecting means has detected the fact that the electrical resistance of the sensing element has crossed a predetermined level.

It is therefore a primary object of the present invention to obviate the disadvantages of the prior art as described above and to provide an improved sensing device.

Another object of the present invention is to provide an improved sensor for sensing the present status of an environment, such as a gas sensor, temperature sensor, humidity sensor or alcohol sensor.

A further object of the present invention is to provide an improved sensing device for sensing the presence of a particular object in an environment, such as a particular gas or vapor, beyond a predetermined level.

A still further object of the present invention is to provide a sensing device reliable in operation and high in performance.

Other objects, advantages and novel features of the present invention will become apparent from the following detailed description of the invention when considered in conjunction with the accompanying drawings.

DESCRIPTION OF THE PREFERRED EMBODIMENTS

Figure 1:
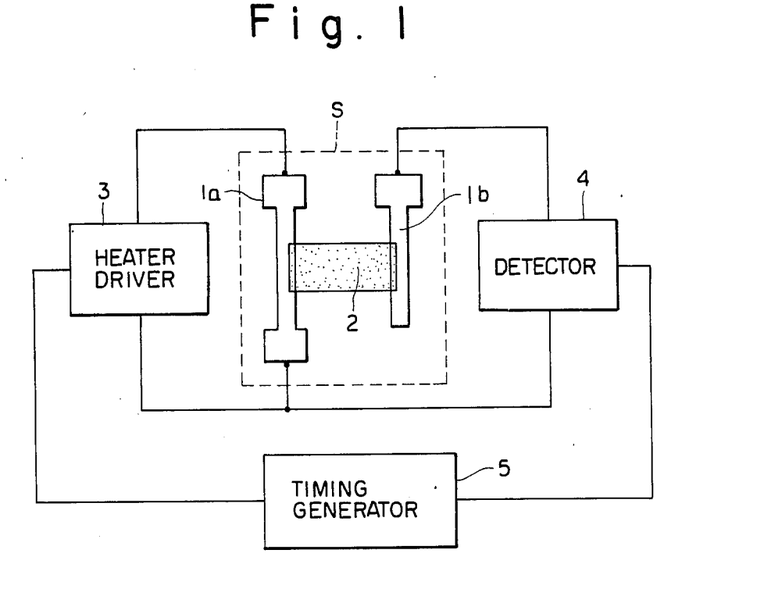
FIG. 1 is a schematic illustration showing a gas sensor constructed in accordance with one embodiment of the present invention.

Referring now to FIG. 1, there is schematically shown a gas sensor constructed in accordance with one embodiment of the present invention. As shown, the gas sensor includes a sensing section S in which a pair of lead strips 1a and 1b are provided in parallel as spaced apart from each other and a sensing element 2 preferably comprised of a metal oxide semiconductor material is provided as extending between the pair of lead strips 1a and 1b in the form of a bridge. Among the pair of lead strips 1a and 1b the lead strip 1a serves not only as an electrode to the sensing element 2, but also as a heater for heating the sensing element 2 to a predetermined temperature. In the preferred embodiment, the sensing element 2 is comprised of $SnO_2$ and it is constructed in the form of a thin film extending between the pair of lead strips 1a and 1b in the shape of a bridge, thereby minimizing its thermal capacity. And, when the sensing element 2 is heated to a predetermined temperature, ranging between 350° and 400° C., by the lead strip 1a also serving as a heater, absorption and release of a particular gas to and from the sensing element 2 takes place. Thus, if a particular gas to be sensed is present in the environment, the gas molecules are absorbed to the sensing element 2, thereby reducing its electrical resistance; whereas, if the particular gas becomes absent or diluted, the gas molecules are released from the sensing element 2, thereby increasing its electrical resistance to the original level. Such changes in electrical resistance across the sensing element 2 are detected by passing a detection current across the sensing element 2.

Both ends of the lead strip 1a serving also as a heater are coupled to a heater driving circuit 3, which applies a driving voltage, for example, of 1.5 to 3 V in the form of pulse is applied to the heater strip 1a, so that a driving current is passed through the lead strip 1a, thereby causing Joule heating. On the other hand, one end of the other lead strip 1b is coupled to a detecting circuit 4 which is also coupled to the bottom end of the lead strip 1a. The detecting circuit 4 is provided with a detection voltage source, for example, of 1.5-3 V. This, when activated, the detecting circuit 4 supplies a detection driving current in the form of pulse to pass through the sensing element 2, whereby the changes in electrical resistance of the sensing element 2 may be detected as changes in voltage across the sensing element 2. It is to be noted that the detection driving current may be continuous, if desired, rather than pulse form.

In accordance with the prior art teaching, while the sensing element 2 is heated by the heater strip 1a, the detection driving current is passed through the sensing element 2 as supplied from the detecting circuit 4. In this case, however, the heater driving current supplied from the heater driving circuit 3 partly leaks through the sensing element 2, so that this lead current tends to decrease the output signal to be detected by the detecting circuit 4. Such a disadvantage is suitably eliminated in accordance with the present invention.

Figure 3:
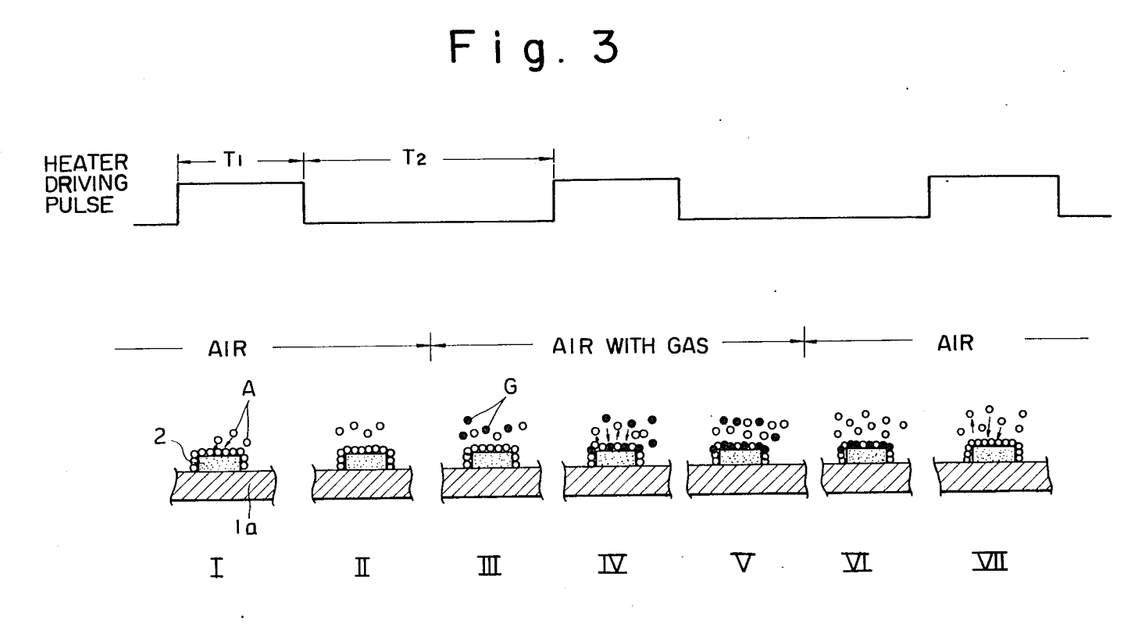
FIG. 3 is a schematic illustration which is useful for explaining the principle of operation of the gas sensor shown in FIG. 1.

Now, the present inventors have found a particular relationship between the temperature of the gas sensing element 2 and the gas absorption/release function with respect to the sensing element 2 as will be discussed in detail below with reference to FIG. 3. As shown, FIG. 3 schematically illustrates how air molecules A and gas molecules G are absorbed by and released from the gas sensing element 2 at various temporal stages I through VII when a heater driving pulse is applied to the heater strip 1a intermittently. Under the condition that only air is present in the environment and no particular gas is present, when a heater driving pulse is applied to the heater strip 1a at the initial temporal stage I, the air molecules A are absorbed to the surface of the gas sensing element 2. Then, at the second temporal stage II, where the heating has been terminated, the temperature of the gas sensing element 2 drops rapidly because it has a small thermal capacity and thus it reaches an equilibrium temperature within 1 millisecond. In this case, even if the temperature of the gas sensing element 2 has lowered, the condition established at the initial stage I is maintained. Under the condition, even if gas molecules enter the environment, since the gas sensing element 2 is at low temperature, its surface condition remains unchanged (third temporal stage III). Thereafter, if the heater driving voltage is again applied and thus the heater 1a is activated to produce heat, the gas sensing element 2 is again heated so that the air molecules A absorbed at the surface of the gas sensing element 2 are released into the environment, and, at the same time, gas molecules G are absorbed to the gas sensing element 2 at those vacated portions, as shown at fourth temporal stage IV. In this case, since the gas sensing element 2 is in the form of a thin film, such an absorption and release operation takes place momentarily. Then, when the heater strip 1a is deactivated, the gas the surface condition established at the fourth temporal stage IV is maintained at the fifth temporal stage V. This condition is maintained even if the environmental condition changes as indicated at the sixth temporal stage VI. Then, when the heater strip 1a is once again activated as indicated at the seventh temporal stage VII, the gas molecules G are released from the gas sensing element 2 and the air molecules A are absorbed to the gas sensing element 2 instead.

As described above, the molecules absorbed at the surface of the gas sensing element 2 while it is heated remains absorbed when the gas sensing element 2 is cooled until the gas sensing element 2 is again heated. In this instance, even if the inter-pulse interval $T_2$, during which the gas sensing element 2 remains lower in temperature, is relatively long, e.g., in the order of 100 minutes, the absorbed condition is little affected. If the gas sensing element 2 is comprised of a metal oxide semiconductor material, such as $SnO_2$, and formed in the shape of a thin film small in thermal capacity, the absorption and release response with respect to the activation and deactivation of the heater strip 1a is excellent, so that the operating condition may be conveniently set with the pulse on time period $T_1$ being set in a range between 1 millisecond and 1 second and the pulse off time period $T_2$ being set in a range between 0.1 seconds and 100 minutes.

Figure 4:
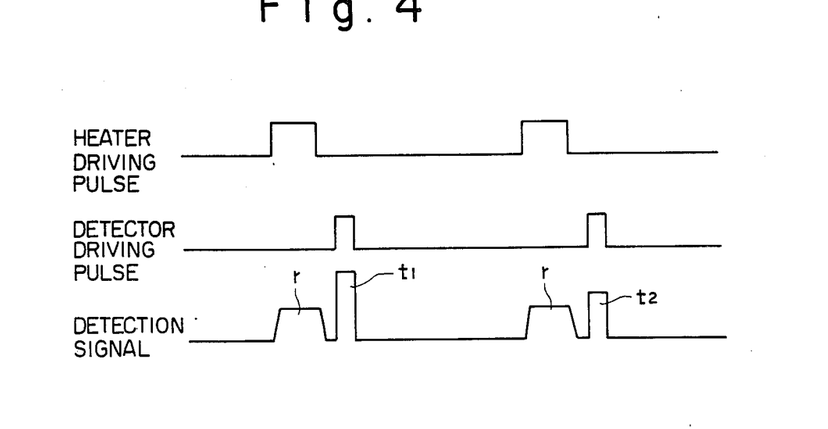
FIG. 4 is a timing chart which is useful for explaining the operation of the gas sensor shown in FIG. 1.

Based on the above finding, as shown in FIG. 4, in accordance with the illustrated embodiment of the present invention, after completion of supply of the heater driving pulse to the heater driving circuit 3, the detection driving pulse is applied to the gas sensing element 2, which retains the gas absorbed condition, so as to obtain a detection signal. With this structure, there are obtained a signal r representing the leakage current due to the heater driving pulse and a desired signal t representing the gas absorbed condition at the surface of the gas sensing element 2 in the detection signal.

Figure 2:
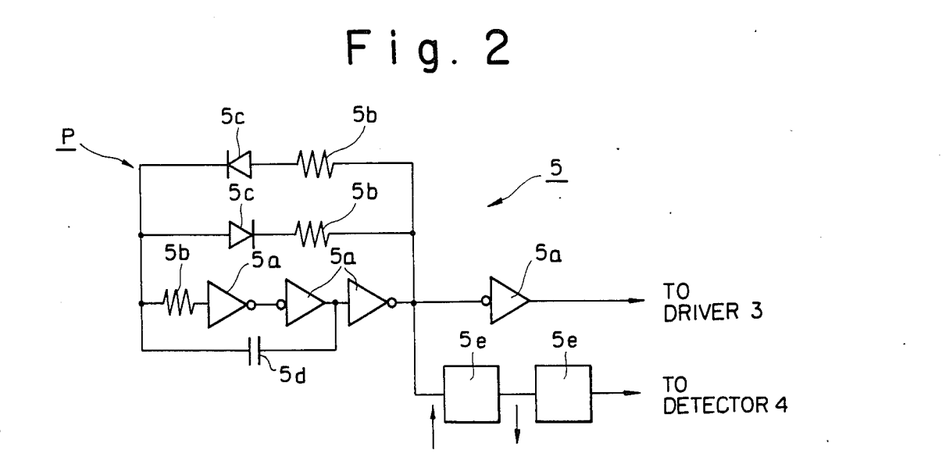
FIG. 2 is a circuit diagram showing the detailed structure of the timing generator provided in the gas sensor of FIG. 1.

In the embodiment shown in FIG. 1, there is provided a timing generator 5 which controls the timing of supplying the heater and detection driving pulses from the heater driving circuit 3 and the detecting circuit 4. As shown in FIG. 2, the timing generator 5 includes a pulse generating circuit P comprised by connecting inverters 5a, resistors 5b, diodes 5c and a capacitor 5d, as shown, and the pulse generating circuit P is connected to the heater driving circuit 3 through an inverter 5a, whereas, the pulse generating circuit P is connected to the detecting circuit 4 through a pair of serially connected monomulti-vibrators 5e, 5e. With this structure, the pulse generating circuit P generates a first pulse signal having a small duty ratio to be supplied to the heater driving circuit 3, which, in turn, creates a second pulse signal shifted in timing over a desired time period through the series-connected pair of monomulti-vibrators 5e, 5e to be supplied to the detecting circuit 4.

In operation, assuming that a particular gas is present in the environment, if the heater driving pulse is applied to the heater driving circuit 3, the gas sensing element 2 is heated to a predetermined temperature, whereby the gas molecules are absorbed to the surface of the gas sensing element 2, which causes the electrical resistance of the gas sensing element 2 to be lowered. In this case, the output signal corresponding to the leakage current component of the heater driving current flowing through the gas sensing element 2 is detected by the detecting circuit 4. However, since no detecting driving pulse is applied at this time, this output signal r is significantly lower than a predetermined level so that no alarm signal is produced.

After termination of the heater driving pulse, the timing generator 5 supplies a timing signal to the detecting circuit 4 at a timing shifted in time as from the timing for activation of the heater driving circuit 3, and in response to this timing signal, the gas sensing element 2 receives the detecting driving pulse supplied from the detecting circuit 4. In this case, the surface condition of the gas sensing element 2 remains the same as the time when the heater driving pulse is applied so that the gas molecules remain absorbed at the surface of the gas sensing element 2. As a result, since the electrical resistance of the gas sensing element 2 is lowered due to the absorption of gas molecules, there is obtained a high output voltage signal $t_1$, which, in turn, generates an alarm signal, indicating the presence of the particular gas in the environment beyond a predetermined level.

Then, it is assumed that the particular gas dissipates from the environment of the gas sensing element 2. However, the surface of the gas sensing element 2 retains the gas molecules until the next heater driving pulse is applied. If the heater driving pulse is applied, the gas sensing element 2 is immediately heated to the predetermined temperature so that the gas molecules are released from the surface of the gas sensing element 2 and at the same time air molecules become absorbed in place thereof, whereby the electrical resistance of the gas sensing element 2 increases to its original value before the absorption of gas molecules. In this case also, an output singal r due to leakage current appears, but this does not have any effect in the operation of the present invention as set forth before. Then, at a timing shifted in time after termination of the heater driving pulse, the detector driving pulse is applied so that there is obtained a detection signal $t_2$. In this case, since the gas sensing element 2 has a large electrical resistance, the level of the output signal $t_2$ is lower in level so that no alarm signal is produced.

As described above, in accordance with this embodiment of the present invention, the heater is activated intermittently and the electrical propertly of the gas sensing element 2 is detected during the time period in which the heater is deactivated, so that there is obtained an output signal having a large S/N ratio and least affected by the leakage current from the heater driving pulse.

Figure 5:
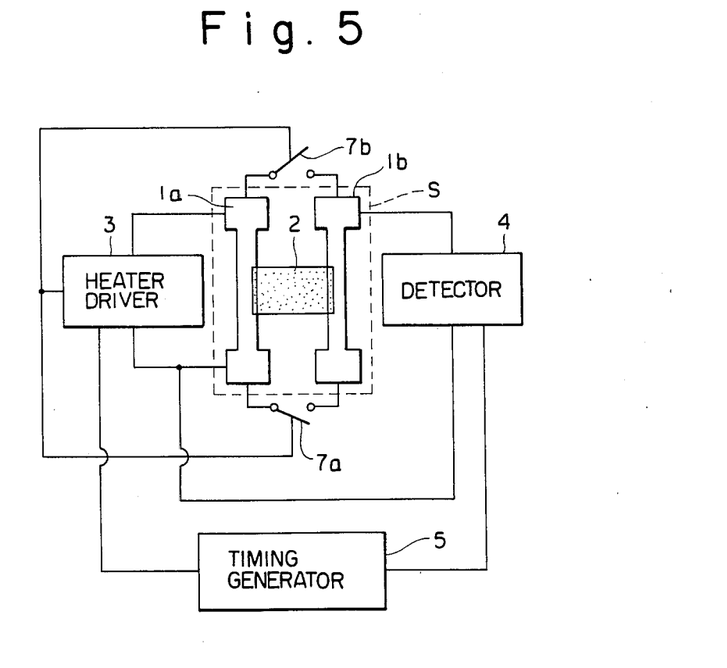
FIG. 5 is a schematic illustration showing a gas sensor constructed in accordance with another embodiment of the present invention.

Referring now to FIG. 5, there is schematically shown a gasdetector constructed in accordance with another embodiment of the present invention. The embodiment shown in FIG. 5 is similar in many respects to the embodiment shown in FIG. 1 so that identical elements are indicated by identical numerals and reference characters. As different from the embodiment shown in FIG. 1, the embodiment shown in FIG. 5 includes a pair of switches 7a and 7b each of which is connected between the corresponding ends of the pair of lead strips 1a and 1b. Each of the switches 7a and 7b is preferably comprised of an electronics switch or a reed switch, which has a high response characteristic. The switches 7a and 7b are set open in normal condition. Both ends of the lead strip 1a are connected to the heater driving circuit 3 and both of the switches 7a and 7b are commonly connected to the heater driving circuit 3. On the other hand, the detector circuit 4 is connected between the pair of lead strips 1a and 1b.

Figure 6:
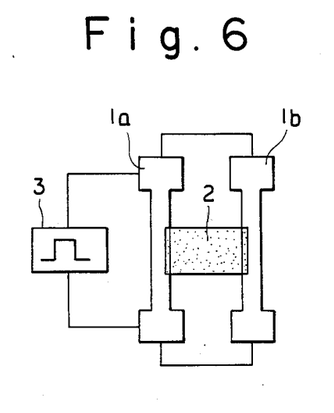
FIGS. 6 and 7 are schematic illustrations which are useful for explaining the operation of the gas sensor shown in FIG. 5.
Figure 7:
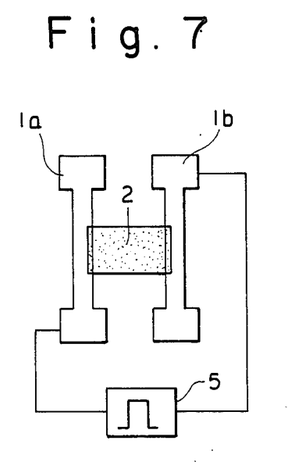
Figure 8:
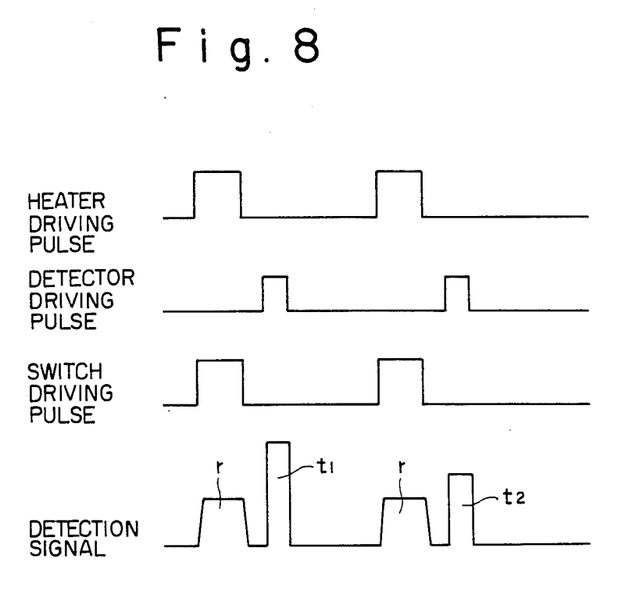
FIG. 8 is a timing chart which is useful for explaining the operation of the gas sensor shown in FIG. 5.

Thus, in the present embodiment, when the gas sensing element 2 is heated to a predetermined temperature, the switches 7a and 7b are closed, thereby connecting the pair of lead strips 1a and 1b in parallel as shown in FIG. 6. Under the condition, the heater driving circuit 3 is activated to pass a heater driving pulse, for example, of 1.5–3 V through both of the lead strips 1a and 1b, whereby both of the lead strips are heated to heat the gas sensing element 2 to a predetermined temperature efficiently as well as uniformly. When the electrical resistance of the gas sensing element 2 is to be detected, the switches 7a and 7b are turned open as shown in FIG. 7 and the detecting circuit 5 suppies a detection driving pulse, for example, of 1.5–3 V to pass through the gas sensing element 2, whereby changes in electrical resistance of the gas sensing element 2 can be detected as changes in voltage across the gas sensing element 2. The operation of the gas sensor shown in FIG. 5 will be understood more fully when reference is made to the timing chart shown in FIG. 8.

Figure 9:
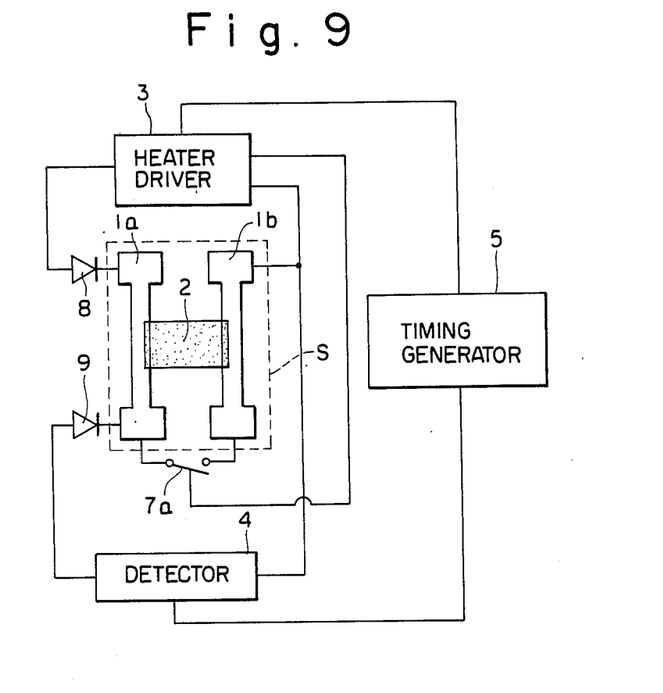
FIG. 9 is a schematic illustration showing a gas sensor constructed in accordance with a further embodiment of the present invention.

FIG. 9 schematically shows a gas sensor constructed in accordance with a further embodiment of the present invention. Since the embodiment shown in FIG. 9 is similar in many respects to the embodiment shown in FIG. 5, identical elements are indicated by identical numerals and reference characters. The present embodiment is so structured that the pair of lead strips 1a and 1b are connected in series when they are used as heater strips. Thus, only one switch 7a is provided as connected bottom ends of the pair of lead strips 1a and 1b, and the top ends of the pair of lead strips 1a and 1b are connected to the heater driving circuit 3. Similarly with the previous embodiment, the detecting circuit 4 is provided as connected between the pair of lead strips 1a and 1b. In the illustrated embodiment, in order to prevent undesired current from flowing in, a diode 8 is connected between the top end of the lead strip 1a and the heater driving circuit 3 and another diode 9 is connected between the bottom end of the lead strip 1a and the detecting circuit 4, as shown.

Figure 10:
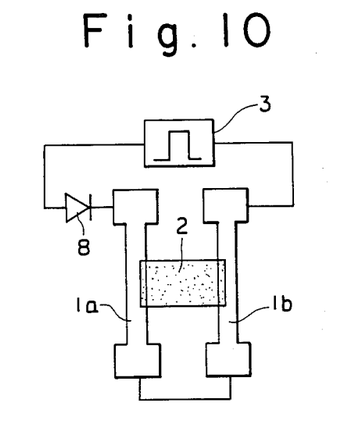
FIGS. 10 and 11 are schematic illustrations which are useful for explaining the operation of the gas sensor shown in FIG. 9.
Figure 11:
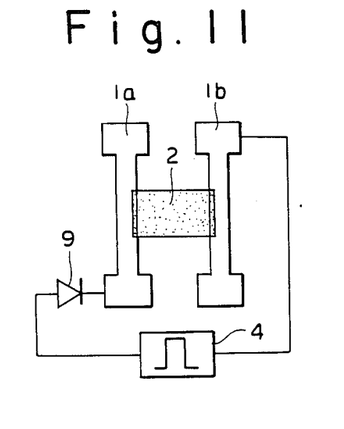

With this structure, when the gas sensing element 2 is to be heated, the switch 7a is closed to establish the structure shown in FIG. 10, whereby both of the lead strips 1a and 1b, which are connected in series, produce heat by Joule heating to heat the gas sensing element 2 from both sides efficiently as well as uniformly. And, during the detection phase, the switch 7a is disconnected to establish the structure shown in FIG. 11 and the detection driving pulse is passed across the gas detecting element 2 to detect the electrical resistance thereof or voltage thereacross.

Figure 12:
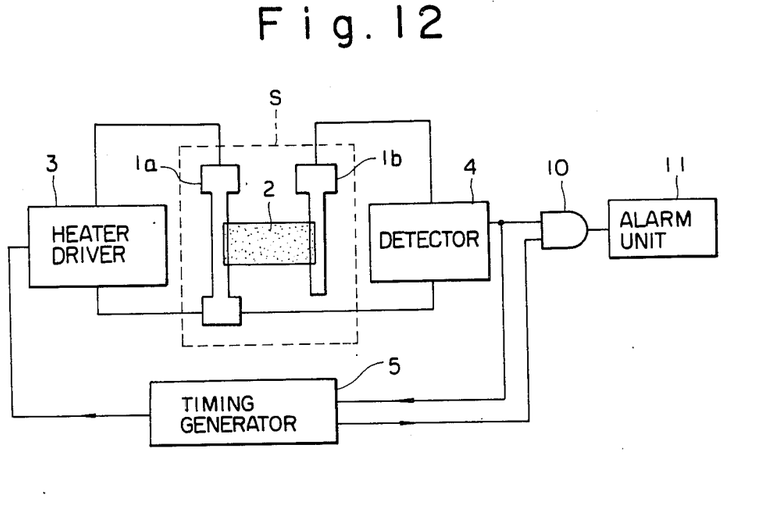
FIG. 12 is schematic illustration showing a gas sensor constructed in accordance with a still further embodiment of the present invention.
Figure 13:
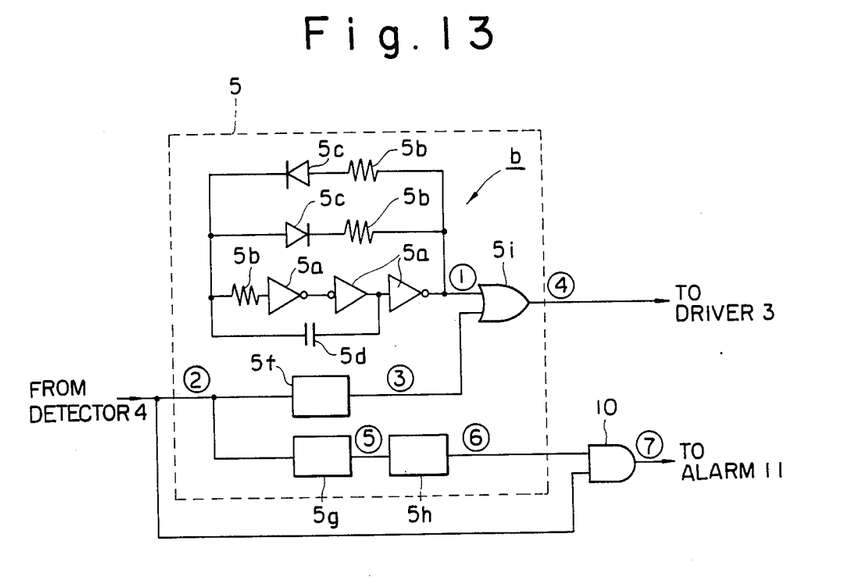
FIG. 13 is a circuit diagram showing the detailed structure of the timing generator provided in the gas sensor shown in FIG. 12.

Referring now to FIG. 12, a still further embodiment of the present invention will be described. As understood, the present embodiment shown in FIG. 12 is structurally similar in many respects to the embodiment shown in FIG. 1, so that identical elements are indicated by identical numerals and reference characters. In the present embodiment, additional elements, including an AND gate 10 and an alarm unit 11, are shown. That is, the AND gate 10 has its one input terminal connected to an output terminal of the detecting circuit 4, its another input terminal connected to the timing generator 5, and its output terminal connected to the alarm unit 11. The timing generator 5 of the present embodiment, however, differs in structure from that of the embodiment shown in FIG. 1 and its detailed structure is shown in FIG. 13. As shown in FIG. 13, the timing generator 5 of the present embodiment shown in FIG. 13 includes a fundamental pulse generating circuit b comprised of inverters 5a, resistors 5b, diodes 5c and a capacitor 5d connected as shown, and the output of the fundamental pulse generating circuit b is connected to the heater driving circuit 3 through an OR gate 5i. The timing generator 5 also includes a first monomulti-vibrator 5f which is connected between the detecting circuit 4 and one input terminal of the OR gate 5i. Also provided in the timing generator 5 include a pair of serially connected second and third monomulti-vibrators 5g and 5h between the detecting circuit 4 and the AND gate 10.

The operation of the gas sensor shown in FIGS. 12 and 13 will be described in detail with reference to the timing chart shown in FIGS. 14a through 14g. It is to be noted that the signals shown in FIGS. 14a through 14g represent those signals which appear at circled number points indicated in FIG. 13.

Figure 14A:
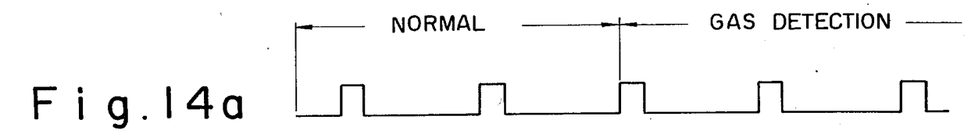
FIGS. 14a through 14g are timing charts which are useful for understanding the operation of the gas sensor shown in FIG. 12.
Figure 14B:
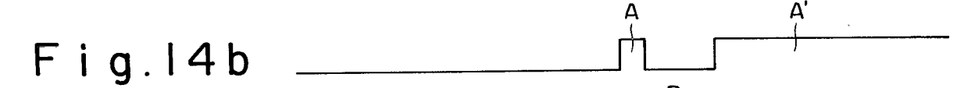
Figure 14C:
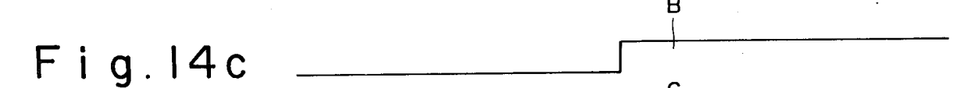
Figure 14D:
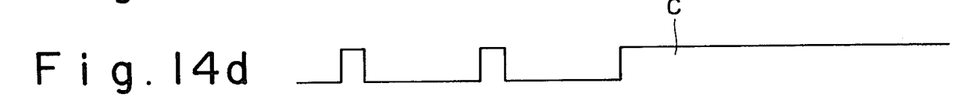
Figure 14E:
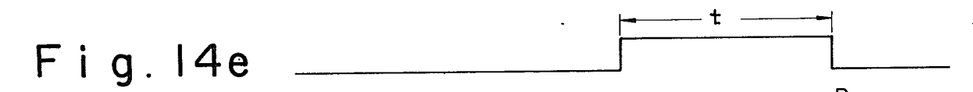
Figure 14F:
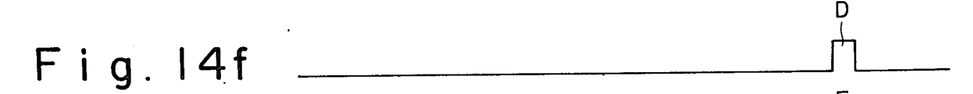
Figure 14G:
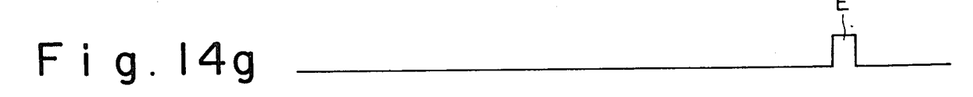

During normal mode, in which no particular gas to be detected is present in the environment of the gas sensing element 2, in order to minimize power consumption, in accordance with a fundamental periodic signal shown in FIG. 14a and obtained at the output of the fundamental pulse generating circuit b indicated by circled number 1, the heater strip 1a is driven or activated intermittently at a regular interval as indicated in FIG. 14d. Under the above-described condition, if the particular gas to be detected flows into the environment of the gas sensing element 2, when the gas sensing element 2 is heated to a temperature in a range between 350°–400° C., the gas molecules become absorbed at the surface of the gas sensing element 2 so that the electrical resistance of the gas sensing element 2 becomed decreased. As a result, its detection signal A appears in the signal indicated in FIG. 14b, which, in turn, causes to activate the first monomulti-vibrator 5f, thereby applying a steady-state on signal B shown in FIG. 14c to the other input terminal of the OR gate 5i. Thus, the OR gate 5i supplies a corresponding steady-state driving signal C to the heater driving circuit 3 so that the heater strip 1a comes to be activated in a steady-state fashion The detection signal A is supplied not only to the first monomulti-vibrator 5f, but also to the second monomulti-vibrator 5g. Then, after elapsing a time period t long enough for obtaining a second stable detection signal A', the second monomulti-vibrator 5g causes the third monomulti-vibrator 5h to be activated so that the third monomulti-vibrator 5h, at this time, outputs an output signal D to one input terminal of the AND gate 10. The AND gate 10 also receives the other input signal from the detecting circuit 4, and it supplies an alarm signal E shown in FIG. 14g to the alarm unit 11 only when the AND condition is satisfied between the two input signals.

While the above provides a full and complete disclosure of the preferred embodiments of the present invention, various modifications, alternate constructions and equivalents may be employed without departing from the true spirit and scope of the invention. For example, the present invention may be applied for sensing various items, such as vapor or powder, and state parameters, such as temperature, or humidity. Therefore, the above description and illustration should not be construed as limiting the scope of the invention, which is defined by the appended claims.

What is claimed is:

1. A sensing device comprising:
a sensing element whose electrical resistance changes depending on a condition of a surrounding environment;
heating means for heating said sensing element to a predetermined temperature;
detecting means for detecting the electrical resistance of said sensing element; and
control means for controlling the activation of said heating means and detecting means such that said detecting means is activated only in a time period in which said heating means is not activated.

2. Device of claim 1 wherein said condition of a surrounding environment includes presence of a particular gas.

3. Device of claim 2 wherein said sensing element includes a metal oxide semiconductor material.

4. Device of claim 3 wherein said metal oxide semiconductor material is $SnO_2$.

5. Device of claim 1 wherein said sensing element is formed in the shape of a thin film.

6. Device of claim 5 further comprising a first lead strip operatively connected to said heating means and a second lead strip operatively connected to said detecting means, wherein said thin-film shaped sensing element is provided to bridge between said first and second lead strips.

7. A sensing device comprising:
a pair of first and second lead strips;
a sensing element whose electrical resistance changes depending on a condition of a surrounding environment, said sensing element extending between said pair of first and second lead strips;
switching means connected between said pair of first and second lead strips;

heating device current applying means for applying a heating drive current to said pair of first and second lead strips;

detecting means for detecting the electrical resistance of said sensing element; and control means for controlling the activation of said switching means, said heating drive current applying means and said detecting means such that said detecting means is activated only in a time period in which said heating means is not activated and that said switching means is closed to connect said pair of first and second lead strips when said heating drive current applying means is activated.

8. Device of claim 7 wherein said condition of a surrounding environment includes presence of a particular gas.

9. Device of claim 8 wherein said sensing element includes a metal oxide semiconductor material.

10. Device of claim 9 wherein said metal oxide semiconductor material is $SnO_2$.

11. Device of claim 7 wherein said pair of first and second lead strips are connected in parallel when said switching means is closed.

12. Device of claim 7, wherein said pair of first and second strips are connected in series when said switching means is closed.

13. A sensing device comprising:

a sensing element whose electrical resistance changes depending on a condition of a surrounding environment;

heating means for heating said sensing element to a predetermined temperature, said heating means having a first heating mode in which heating is carried out periodically and a second heating mode in which heating is carried out continuously;

detecting means for detecting the electrical resistance of said sensing element, said detecting means supplying a preliminary signal when said electrical resistance has reached a predetermined state; and control means for controlling the mode of operation of said heating means such that said heating means normally operates in said first heating mode and said heating means changes from said first heating mode to said second heating mode in response to said preliminary signal supplied from said detecting means.

14. Device of claim 13 wherein said condition of a surrounding environment includes presence of a particular gas.

15. Device of claim 14 wherein said sensing element includes a metal oxide semiconductor material.

16. Device of claim 15 wherein said metal oxide semiconductor material is $SnO_2$.

* * * * *